(12) United States Patent
Nasca et al.

(10) Patent No.: US 11,849,976 B1
(45) Date of Patent: Dec. 26, 2023

(54) SCOLIOSIS SUPPORT ROD SYSTEM

(71) Applicants: Richard Nasca, Wilmington, NC (US);
Robert Assell, St. Paul, MN (US);
Andy Freeman, Roseville, MN (US)

(72) Inventors: Richard Nasca, Wilmington, NC (US);
Robert Assell, St. Paul, MN (US);
Andy Freeman, Roseville, MN (US)

( * ) Notice: Subject to any disclaimer, the term of this patent is extended or adjusted under 35 U.S.C. 154(b) by 0 days.

(21) Appl. No.: 17/684,835

(22) Filed: Mar. 2, 2022

Related U.S. Application Data

(60) Provisional application No. 63/157,117, filed on Mar. 5, 2021.

(51) Int. Cl.
*A61B 17/70* (2006.01)

(52) U.S. Cl.
CPC ...... *A61B 17/7031* (2013.01); *A61B 17/7025* (2013.01)

(58) Field of Classification Search
CPC ................. A61B 17/7031; A61B 17/7025
See application file for complete search history.

(56) References Cited

U.S. PATENT DOCUMENTS

| | | | | |
|---|---|---|---|---|
| 8,043,340 B1* | 10/2011 | Law | ................... | A61B 17/7032 606/257 |
| 10,639,078 B2* | 5/2020 | Williams | ............. | A61B 17/705 |
| 2010/0211104 A1* | 8/2010 | Moumene | .......... | A61B 17/7028 606/264 |
| 2012/0310285 A1* | 12/2012 | Zhao | ................... | A61B 17/705 606/264 |

* cited by examiner

*Primary Examiner* — Tessa M Matthews
(74) *Attorney, Agent, or Firm* — Spencer Fane, LLP

(57) ABSTRACT

A scoliosis support rod system for treating scoliosis in a spine having a first vertebra and a second vertebra. The scoliosis support rod system includes a central rod segment, a first end rod segment, a first bone anchor and a second bone anchor. The central rod segment has a first end and a second end. The central rod segment is deformable in response to a force placed thereon. The central rod segment returns to an initial configuration when the force is discontinued. The first end rod segment has a first aperture formed therein. The first aperture is adapted to slidably receive the first end of the central rod segment. The first bone anchor is attachable to the first end rod segment. The first bone anchor is attachable to the first vertebra. The second bone anchor is attachable to the central rod segment. The second bone anchor is attachable to the second vertebra. When the first bone anchor is attached to the first vertebra and the second bone anchor is attached to the second vertebra, a length of the scoliosis support rod system is adjustable by sliding the central rod segment with respect to the first end rod segment.

20 Claims, 4 Drawing Sheets

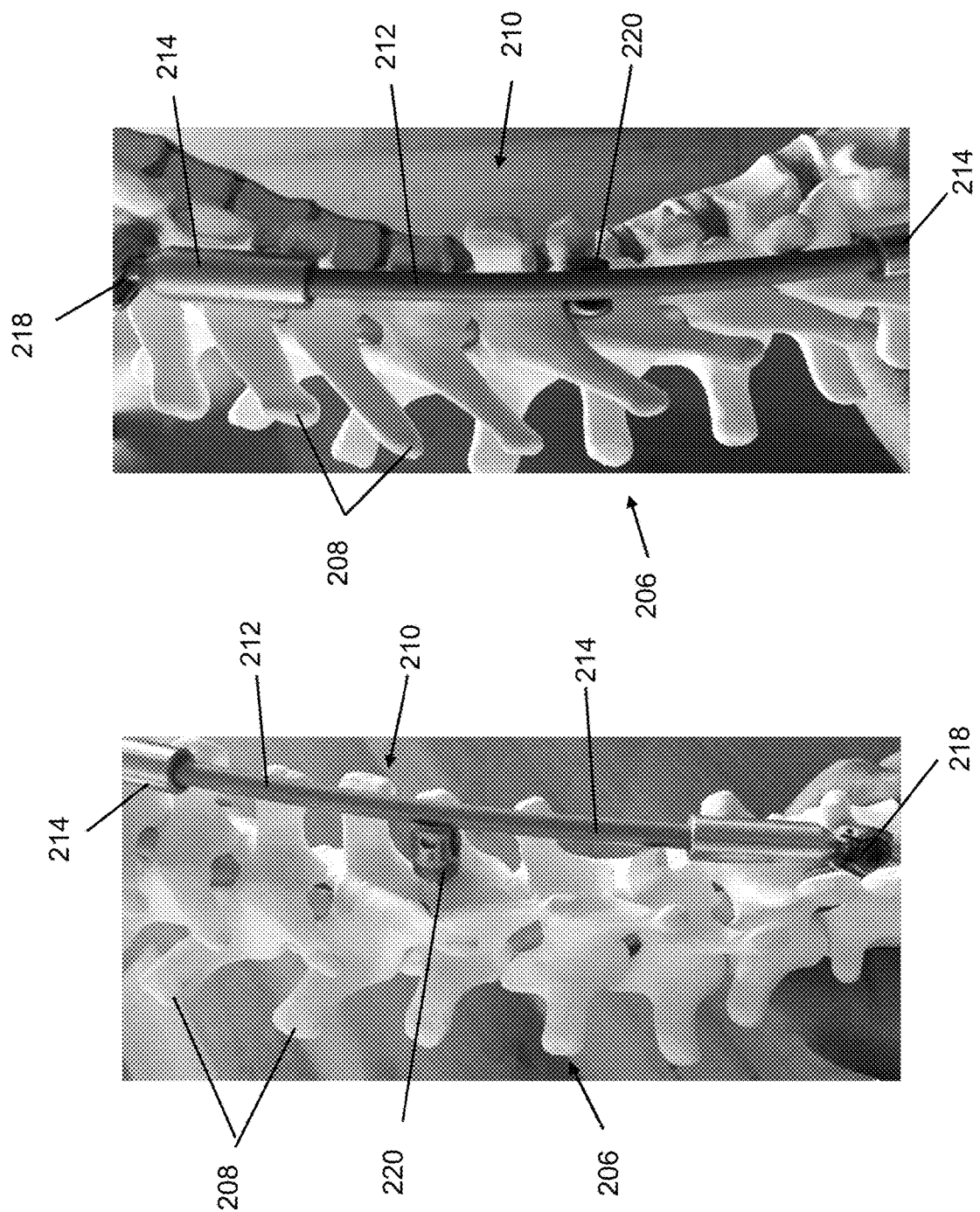

SCOLIOSIS SUPPORT ROD SYSTEM

REFERENCE TO RELATED APPLICATION

This application claims priority to Provisional Application No. 63/157,117, filed on Mar. 5, 2021, the contents of which are incorporated herein by reference.

FIELD OF THE INVENTION

The invention relates generally to treatments for scoliosis. More particularly, the invention relates to a scoliosis support rod system.

BACKGROUND OF THE INVENTION

Adolescent Idiopathic Scoliosis ("AIS") is characterized by a lateral curvature of the spine. It is typically seen in children, ages 10-15. AIS is eight times more common in females than males. The cause of AIS is unknown although genetics may play a role in 30 percent. Abnormalities in the vertebral growth plates may be responsible for uneven longitudinal growth of the vertebrae leading to a lateral spine curvature with abnormal rotation and loss of the normal sagittal curves of thoracic kyphosis and lumbar lordosis Curves may be mild (10-20 degrees), moderate (20-45 degrees) and severe (over 50 degrees). There are several types of curves with the most common being a right thoracic, Lenke type 1 and thoracolumbar/lumbar, Lenke type 5.

Approximately 2-3 percent of the general population of children are affected by scoliosis. They may require some type of treatment such as observation, physical therapy, bracing or surgery. Braces are fitted for about 30,000 patients each year and surgery is done on about 38,000 patients each year. About 80 percent of cases are due to AIS and about 10-15 percent of cases are due to juvenile scoliosis seen in children ages four through nine.

Observation is recommended for curves less than 25 degrees or in children who have stopped growing and have curves that are not changing. Physical and X-ray evaluations are done every 4 to 6 months to monitor curve progression.

Physical therapy, yoga and chiropractic manipulation have not prevented curve progression but may help strengthen core muscles and manage pain.

Bracing is prescribed for curves larger than 25 degrees but smaller than 45 degrees in children who are still growing. The underarm Boston brace, Thoracolumbar Sacral Orthosis, ("TLSO") and the Milwaukee Brace, a full body brace with a neck ring, mandibular pad, front and back longitudinal bars attached to a molded pelvic girdle are the most commonly prescribed braces. To be effective the patient must wear the brace at least 13 hours a day.

Surgery is recommended for patients with curves usually greater than about 45 degrees and/or who are at high risk of continued worsening even after they are finished growing. There are currently several surgical options for treating scoliosis.

Non-fusion correction with Vertebral Body Tethering ("VBT") uses multiple vertebral body screws placed by open thoracotomy or by percutaneous insertion using an endoscopic approach on the convex side of the curve. A flexible polyethene-terephthalate cord is attached to each screw and as the cord is tightened the screws are compressed and the scoliosis is corrected. A chest tube is used for 48 hours or more following surgery. VBT can be complicated by blood loss, neurologic injury, screw loosening, breakage of the tether and under and over correction of the curve. Conversion to spinal fusion with posterior rod and screw instrumentation is reported to be 20-40 percent of those treated with VBT.

Growing rods and Magnetic Expansive Control System ("MAGEC") rods are used in younger patients with scoliosis due to congenital bony deformities such as hemivertebrae and hemivertebrae with osseous bars and other types of scoliosis associated with various syndromes, (Syndromic scoliosis). Children with neuromuscular, infantile and juvenile scoliosis are candidates for growing rod treatment. The growing rods require repeated trips to the operating room for adjustments and exchange to keep up with the child's spinal growth. The MAGEC rods can be lengthened using an electromagnet in the prone awake patient in an office setting. Most patients treated with growing rods and MAGEC rods will require a spinal fusion with instrumentation as they complete their adolescent growth spurt.

Another non-fusion correction uses the APIFIX (Mid-C System) a concave rod which is secured to the spine with 2 or more pedicle screws. It has a ratchet mechanism that allows for lengthening with growth and performs as an internal brace. Polyaxial mobility is provided by spherical rings attached to pedicle screws allowing up to 40 degrees of rotation. Of the 252 patients treated, close to 20 percent required reoperation. Reoperations were done for device malfunction, nut loosening, misplaced pedicle screws, screw pull out, screw failure, rod fracture and infection. The device costs $25,000 and clinical trials under Humanitarian Device Exception have begun recently in the USA.

Instrumentation and fusion is a definitive treatment to correct and halt the progression of scoliosis. The surgery is done through a long posterior incision and requires stripping of the posterior spinal musculature. Removal of the spinous processes, portions of the facets and various ligaments are done to facilitate correction of the deformity using dual longitudinal rods attached to multiple pedicle screws placed in the vertebrae of the major curve.

To promote fusion, bone grafts and bone graft extenders are added to the decorticated laminae, facets and transverse processes. Surgical complications include excessive blood loss, protentional for neural and spinal cord injury, infection, failure to achieve fusion and rod breakage and screw loosening. Within 2 years following the index surgery nearly 10 percent of operated patients require reoperation. Many patients later in life experience pain in areas distal and proximal to the spinal fusion due to degenerative changes resulting from stress transfer from the fused areas of the spine.

SUMMARY OF THE INVENTION

An embodiment of the invention is directed to a scoliosis support rod system for treating scoliosis in a spine having a first vertebra and a second vertebra. The scoliosis support rod system includes a central rod segment, a first end rod segment, a first bone anchor and a second bone anchor. The central rod segment has a first end and a second end. The central rod segment is deformable in response to a force placed thereon. The central rod segment returns to an initial configuration when the force is discontinued. The first end rod segment has a first aperture formed therein. The first aperture is adapted to slidably receive the first end of the central rod segment. The first bone anchor is attachable to the first end rod segment. The first bone anchor is attachable to the first vertebra. The second bone anchor is attachable to the central rod segment. The second bone anchor is attachable to the second vertebra. When the first bone anchor is attached to the first vertebra and the second bone anchor is attached to the second vertebra, a length of the scoliosis support rod system is adjustable by sliding the central rod segment with respect to the first end rod segment.

Another embodiment of the invention is directed to a scoliosis support rod system for treating scoliosis in a spine having a first vertebra and a second vertebra. The scoliosis support rod system includes a central rod segment, a first end rod segment, a second end rod segment, a first bone anchor and a second bone anchor. The central rod segment has a first end and a second end. The central rod segment is deformable in response to a force placed thereon. The central rod segment returns to an initial configuration when the force is discontinued. The first end rod segment has a first aperture formed therein. The first aperture is adapted to slidably receive the first end of the central rod segment. The second end rod segment has a second aperture formed therein. The second aperture is adapted to slidably receive the second end of the central rod segment. The first bone anchor is attachable to the first end rod segment. The first bone anchor is attachable to the first vertebra. The second bone anchor is attachable to the second end rod segment. The second bone anchor is attachable to the second vertebra.

Another embodiment of the invention is directed to a method of treating scoliosis. A central rod segment having a first end and a second end is provided. A first end rod segment is attached to a first vertebra using a first bone anchor. The first end rod segment has a first aperture formed therein. The first end of the central rod segment is inserted into the first aperture on the first end rod segment. The central rod segment slides with respect to the first end rod segment. The central rod segment is attached to a second vertebra using a second bone anchor so that a force is placed on the central rod segment. The force causes the central rod segment to deform. The force from the central rod segment is transferred to the first bone anchor and the second bone anchor. The force on the first bone anchor and the second bone anchor causes the first vertebra to move away from the second vertebra, which reduces a curvature of a spine in which the first vertebra and the second vertebra are located.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 7 is an alternative configuration of the scoliosis support rod system attached to the spine.

FIG. 8 is another view of the spine with the scoliosis support rod system of FIG. 7.

DETAILED DESCRIPTION OF THE INVENTION

Figure 1:
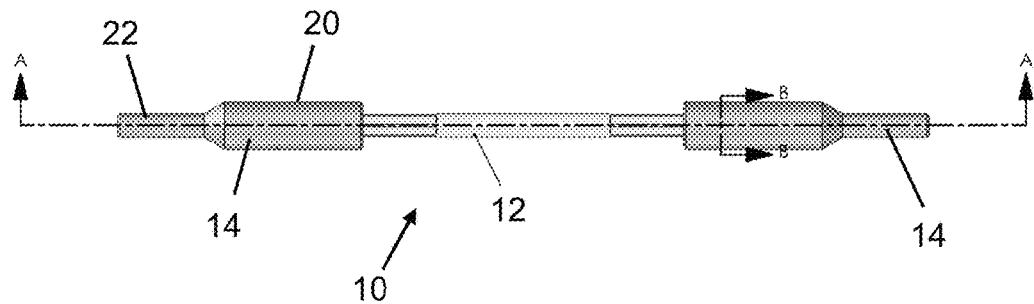
FIG. 1 is a side view of a scoliosis support rod according to an embodiment of the invention.
Figure 2:
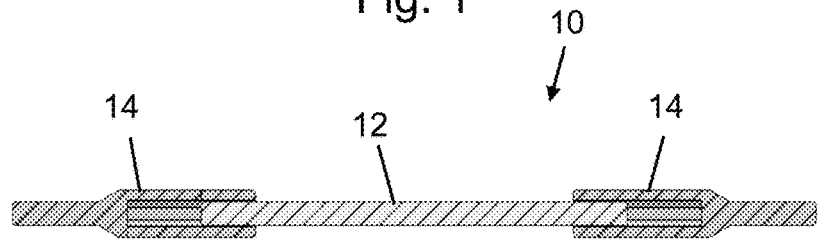
FIG. 2 is a sectional view of the scoliosis support rod taken along a line A-A in FIG. 1.
Figure 3:
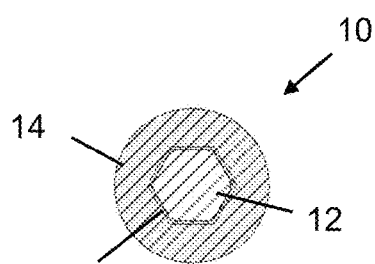
FIG. 3 is a sectional view of the scoliosis support rod taken along a line B-B in FIG. 1.
Figure 4:
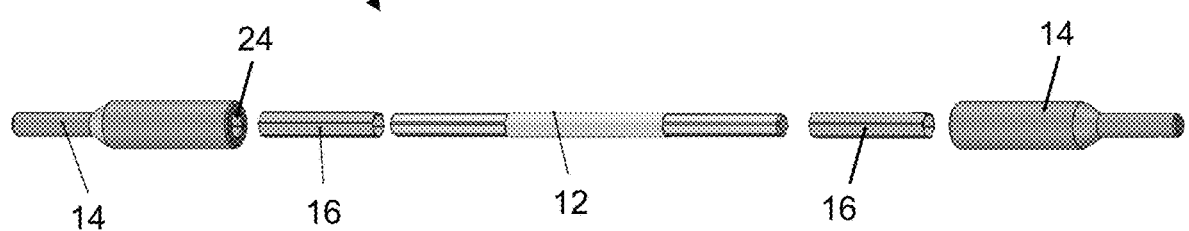
FIG. 4 is an exploded perspective view of the scoliosis support rod.

An embodiment of the invention is directed to a scoliosis rod support system as illustrated at 10 in FIGS. 1-4. The scoliosis support rod system 10 is much less invasive than the surgical treatments for scoliosis that are discussed above. The scoliosis support rod system 10 enables patients with a spinal curvature in the range of about 45 degrees to about 65 degrees to realize significantly reduced spinal curvature without spinal fusion.

The scoliosis support rod system 10 is designed to allow for the adolescent's growth and will provide support and guidance for correction of the scoliosis during a treatment period that is typically between about 18 and 24 months. In other embodiments, the scoliosis support rod system 10 may be used for a longer treatment period such as up to about 6 years.

The scoliosis support rod system 10 is designed to have just one or possibly two degrees of freedom. This means the only unconstrained motion is lateral bending with one degree of freedom or lateral bending and rotation about the long axis with two degrees of freedom. In contrast, conventional surgical treatments for scoliosis involve constraining all 6 degrees of freedom.

After the scoliosis support rod system 10 is implanted, as the spine grows the scoliosis support rod system 10 will lengthen while being rigid with respect to lateral bending. This configuration will direct the spine to straighten out. The action of the scoliosis support rod system 10 is analogous to a length of rope that is initially laid out flat in an S-shape. As the ends of the rope are pulled apart, effectively lengthening the rope, the rope will straighten out.

An expectation of the end result of the scoliosis support rod system treatment is that the spine will not be perfectly straight. Rather, the scoliosis support rod system treatment will provide a significant degree of straightening of the spine as compared to before applying the system. With growth, the scoliosis support rod system 10 would be expected to continue correction of the curvature with the final result being a spine with some residual curvature but to a degree that is cosmetically and functionally acceptable.

A significant benefit of the scoliosis support rod system 10 when compared to conventional scoliosis surgery is the patient has no fusion of any spinal motion segments and the original surgery is dramatically less invasive and traumatic. These benefits enable the patient to a much faster recovery from surgery and less cosmetic scarring.

The scoliosis support rod system 10 allows unrestricted lengthening even with the scoliosis support rod system 10 being subjected to significant lateral bending. The scoliosis support rod system 10 allows relative movement between a central rod segment 12 and at least one end rod segment 14 that engages at least one end of the central rod segment 12.

The central rod segment 12 has an elongated configuration. At least an end of the central rod segment 12 that engages the end rod segment 14 may have a size and a shape that is similar to a size and a shape of an aperture 24 that is formed in an end of the end rod segment. Forming the end of the central rod segment 12 with a shape and a size that is similar to a size and a shape of the aperture 24 facilitates the end rod segment 14 sliding with respect to the central rod segment 12.

While the figures illustrate that the scoliosis support rod system 10 includes two end rod segments 14, it is possible for the invention to only use one end rod segment 14. In such a configuration, the end of the central rod segment 12 to which the end rod segment 14 does not extend over is anchored to the patient's vertebrae.

The depth of the aperture 24 impacts a length of the scoliosis support rod system 10 can be adjusted. Factors that impact the desired length that the scoliosis support rod system 10 is to be adjusted is impacted by factors such as the growth stage of the patient when the scoliosis support rod system 10 is implanted.

In certain embodiments, the end rod segment has a hexagonal shape. A person of skill in the art will appreciate that alternative shapes may be used. Examples of the alternative shapes are circular, triangular, square and oval.

The end rod segment 14 includes a first end 20 and a second end 22. The aperture 24 is formed in the first end 20. To accommodate the insertion of the end of the central rod segment 12 into the aperture 24, a diameter of the first end 20 may be larger than a diameter of the second end. An outer surface of the first end 20 may be generally cylindrical as illustrated in the figures.

An outer surface of the second end 22 may be formed with a shape and a size of a fixation device (illustrated in FIG. 6) that is intended to be used with the scoliosis support rod system 10. In certain embodiments, the outer surface of the second end 22 may have a hexagonal shape. A person of skill in the art will appreciate that the concepts of the invention may be adapted for use with alternative shapes of the second end 22.

In certain embodiments, a sleeve 16 or bushing is provided at least one of the ends of the central rod segment 12. The sleeve 16 acts as a low friction linear bearing between the translating segments.

In certain embodiments, the sleeve 16 is at least partially fabricated from PEEK. PEEK is very lubricious, resists deformation under load, is dimensionally stable and very biocompatible. Deformation under load is critical to prevent cold flow of the material as the sleeve 16 will be continuously subjected to significant bending loads. Dimensional stability is important as the PEEK sleeve 16 is both a linear bearing and a seal to prevent body fluids from entering and affecting the two sliding mechanisms.

In certain embodiments, the central rod segment 12 is at least partially fabricated from NITINOL. This material provides some degree of compliance, which is important for the long-term success of the procedure. A completely rigid construct, i.e., all components made from high tensile materials (such as cobalt chrome alloy, titanium alloy or hardened stainless steel) would transfer all of the bending stress to the screws affixing the system to the spine. This stress can easily cause the failure of the screw's fixation to the patient's bone.

This mechanism is how current generation scoliosis systems rod typically fail. By including a somewhat compliant element in the scoliosis support rod system, stresses associated with daily activity and stress from the growth of the spine keep from over-loading the fixation screws. Such a process is similar to a suspension system in a car.

An additional benefit takes advantage of the lack of stress relaxation inherent in NITINOL. The NITINOL central rod segment 12 will relentlessly work to return to its original straight configuration. In doing so, the central rod segment 12 will push back on the spine causing the spine to move towards being straighter. The end result is exactly analogous to orthodontia, where the constant tension from braces causes teeth to move in a direction that reduces stress and the bone anchoring the teeth gradually remodels (in accordance with Wolff's law) allowing the tooth to rotate and reposition. In this invention, there will be constant tension with the degree of tension determined by the growth rate of the patient, that constantly pushes the spine towards straightness.

The scoliosis support rod system may be implanted through a small incision at the apex on the concave side of the scoliosis. The device is then tunneled under the fascia overlying the paraspinal muscles to connect into the percutaneously placed pedicle screws at the upper and lower vertebrae of the major curve.

Manual pressure applied to the convex side of the curve coupled with distraction of the scoliosis support rod system 10 by the surgeon should result in further correction of these flexible AIS curves. The end rod segment 14 is locked into the bone anchors 18, but is designed to elongate 50 mm with spinal growth. As the vertebrae within the curve grow, the scoliosis support rod system 10 will support coupled forces to further correct the scoliosis. If there should be failure of any of the components in the scoliosis support rod system 10, the scoliosis support rod system 10 can be easily removed and a fusion with traditional instrumentation can be performed.

Additionally, the configuration of the scoliosis support rod system 10 enables the components of the scoliosis support rod system 10 to be removed from the patient using relatively small incisions after the treatment process is complete. In certain situations, the treatment process is between about 5 and 6 years.

Figure 5:
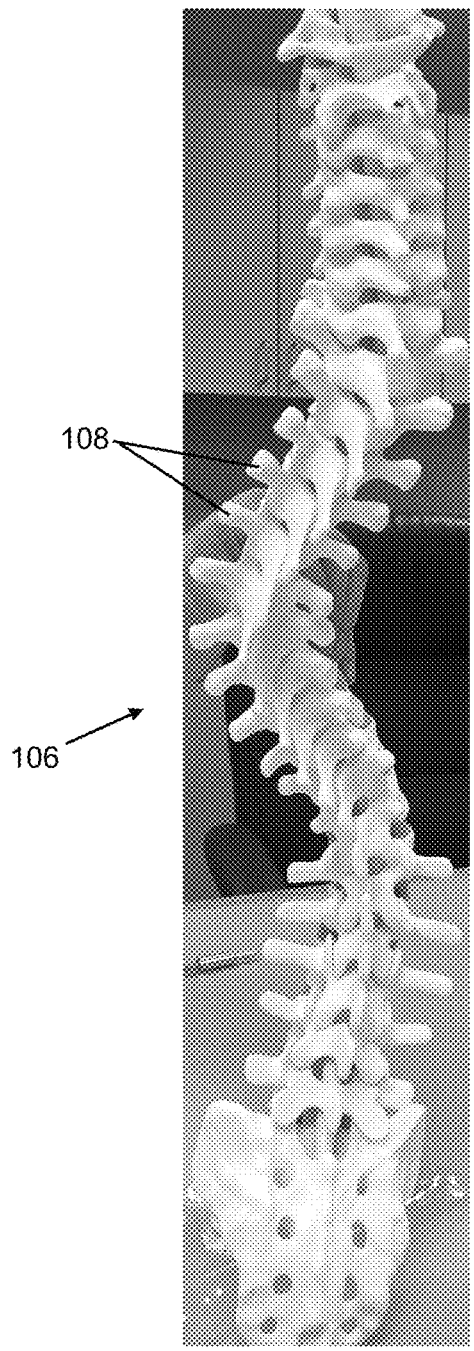
FIG. 5 is a spine that has been deformed by scoliosis.
Figure 6:
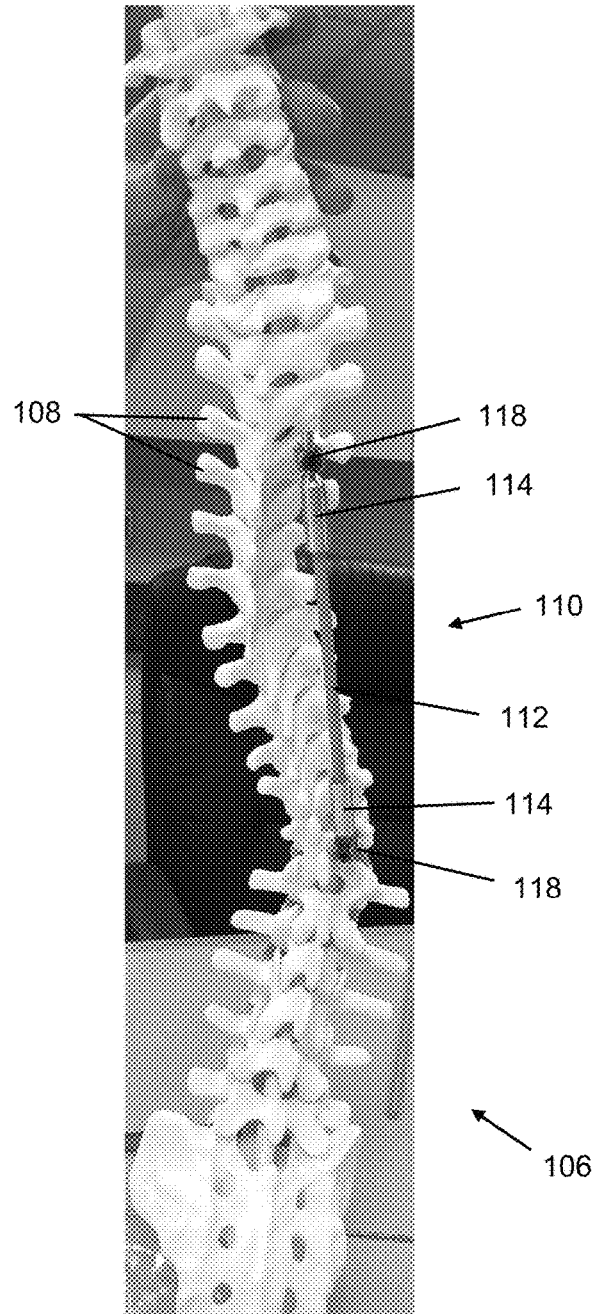
FIG. 6 is the spine of FIG. 5 after treatment with the scoliosis support rod system.
Figure 9:
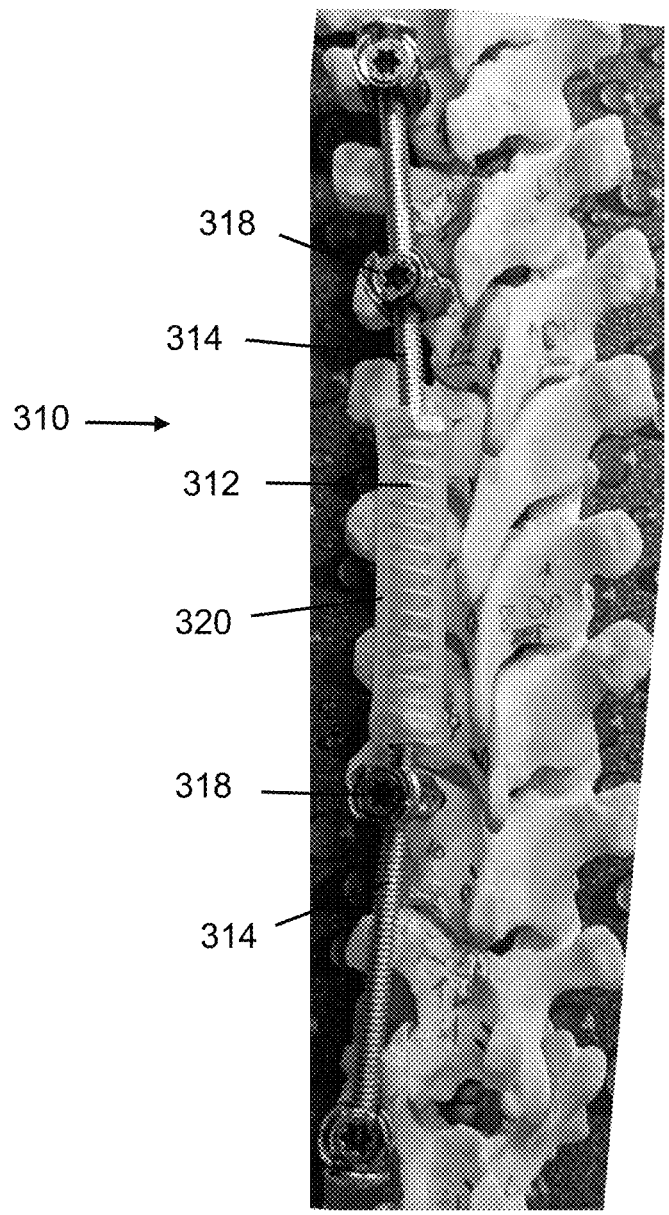
FIG. 9 is an alternative configuration of the scoliosis support rod system.

Use of the scoliosis support rod system 110 is described with respect to a spine 106 illustrated in FIGS. 5 and 6. When the spine 106 has undergone scoliosis, the spine 6 may not only have a curvature in a vertical direction but the spine 106 may also have a rotation such that vertebrae 108 proximate a lower end of the spine 106 are oriented in a different direction than the vertebrae 108 proximate an upper end of the spine 106.

A location of the scoliosis in the spine 106 determines where the scoliosis support rod system 10 is attached to the spine 106. In many situations, the scoliosis support rod system 110 is attached in a thoracic region of the spine 106. However, it is also possible to use the scoliosis support rod system 110 in a cervical region or a lumbar region of the spine 106.

Bone anchors 118 are secured to the vertebrae 108 proximate to upper and lower ends of a section of the spine 106 where scoliosis is being treated. A person of skill in the art will appreciate that a variety of techniques may be used to secure the bone anchors 118 to the vertebrae. An example of one suitable technique is a threaded screw.

Opposite ends of the central rod segment 112 are extended into apertures 124 in the end rod segment 114 and the end rod segments 114 are secured to the bone anchors 118 as illustrated in FIG. 6. A person of skill in the art will appreciate that a variety of techniques may be used to secure the end rod segment 114 to the bone anchors 118.

The attachment of the components of the scoliosis support rod system 110 to the vertebrae 108 is done so that there is a force on the vertebrae 108 to which the bone anchors 108 are attached. This force urges the spine 106 from the initial more curved configuration illustrated in FIG. 5 to the spine less curved configuration illustrated in FIG. 6.

Depending on the material from which the central rod segment 112 is formed, the force applied when implanting the scoliosis rod support system 10 may cause the central rod segment 112 to deform from an initially straight configuration. Examples of suitable materials that may be used to fabricate the central rod segment 112 include NITINOL and PEEK.

The memory of the material from which the central rod segment 112 is formed thereby urges the central rod segment 112 to return to the initial straight configuration and the force associated with such movement causes the curvature of the spine 106 to be reduced such as evidenced by the reduced curvature of the spine 106 illustrated in FIG. 6 as compared to the spine 106 illustrated in FIG. 5.

Additionally, the memory of the material from which the central rod segment 112 is formed thereby urges the central rod segment 112 to return to the initial straight configuration and the force associated with such movement causes derotation of the spine 106, such as evidenced by the configuration of the spine 106 illustrated in FIG. 6 as compared to the spine 106 illustrated in FIG. 5.

A significant benefit of the central rod segment 112 sliding with respect to the end rod segment 114 is that the scoliosis support rod system 110 can change length while the scoliosis support rod system 110 is attached to the spine 106. Increasing the length of the scoliosis support rod system 110 is particularly important when used for treating scoliosis in adolescence that are still growing. Because the scoliosis support rod system 110 reduces the scoliosis while the adolescent person is growing, the person will undergo fewer surgeries to adjust the scoliosis support rod system 110 and/or replace components of the scoliosis support rod system 110 as the person grows.

In certain embodiments, the central rod segment 112 is slidable up to about 3 centimeters with respect to each of the end rod segments without experiencing a degradation of the scoliosis reduction benefits of the scoliosis support rod system 110. The invention thereby accommodates growth of the adolescent person of up to 6 centimeters prior to a revision surgery being needed to lengthen the scoliosis support rod system 110.

While the spine configuration illustrated in FIG. 6 may not be as straight as a spine that has not experienced scoliosis, the spine configuration illustrated in FIG. 6 is sufficiently straight such that the spine curvature does not negatively impact the person's ability to move, such that the person is able to move similar to the movement of a person without scoliosis.

Another benefit of the spine configuration illustrated in FIG. 6 is that the spine 106 is sufficiently straight such that from a cosmetic perspective, it is not possible for other persons to see that the person with the spine configuration illustrated in FIG. 6 has scoliosis.

In contrast to the embodiment of the scoliosis support rod system 10 illustrated in FIGS. 1-4 where the central rod segment 12 has a hexagonal profile, the central rod segment 112 illustrated in FIG. 6 has a substantially cylindrical profile. The circular profile of the central rod segment 112 permits the central rod segment 112 to rotate and slide with respect to each of the end rod segments 114. In contrast, the configuration of the central rod segment 12 illustrated in FIGS. 1-4 only permits the central rod segment 12 to slide with respect to the end rod segments 14.

The configuration of the central rod segment 112 illustrated in FIG. 6 may thereby provide beneficial results where the scoliosis rotation of vertebrae 108 in addition to curvature of the spine 106.

Another embodiment of the invention is illustrated in FIGS. 7 and 8. The scoliosis support rod system 210 of this embodiment is similar to the scoliosis support rod system 10 described with respect to FIG. 6. However, this embodiment of the scoliosis support rod system 210 also includes an intermediate bone anchor 220. The intermediate bone anchor 220 is attached to one of the vertebra 208 that are intermediate the vertebrae 208 to which the bone anchors 218 are attached. While it is illustrated that the intermediate bone anchor 220 is positioned approximately an equal distance between each of the bone anchor 218, alternative configurations are possible. A person of skill in the art will appreciate that a variety of techniques may be used to secure the intermediate bone anchor 120 to the vertebra. An example of one suitable technique is a threaded screw.

The intermediate bone anchor 220 may have a slot formed therein that is adapted to at least partially receive the central rod segment 212. In one configuration, the slot has a depth that is approximately equal to a width of the central rod segment 212. In certain configurations, after implantation, the central rod segment 212 is slidable with respect to the intermediate bone anchor 220. In other configurations, a fixation device may be used to secure the central rod segment 212 in a stationary position with respect to the intermediate bone anchor 220.

The presence of the intermediate bone anchor 220 may in certain situations enhance the ability of the scoliosis support rod system 210 to reduce the severity of the scoliosis, such as reducing the spine curvature and/or derotating the vertebrae 208.

In certain embodiments, an initial axial alignment of the intermediate bone anchor 220 is different than an initial axial alignment of at least one of the end bone anchors 218. In other embodiments, the initial axial alignment of the intermediate bone anchor 220 is different than the initial axial alignment of both of the end bone anchors 218.

An alternative embodiment of the scoliosis support rod system 310 is illustrated in FIG. 5. The scoliosis support rod system 310 generally includes central rod segment 312 that is fabricated from a spring or other similar material that has the ability to change in length in response to a force placed thereon.

A sleeve 320 may be positioned over at least a portion of the central rod segment 312. In certain embodiments, the sleeve 320 substantially covers the central rod segment 312. The sleeve 320 thereby prevents tissue and/or fluid from entering the central rod segment 312 as such tissue and/or fluid may impact the ability of the central rod segment 312 to change length.

Opposite ends of the central rod segment 312 are attached to end rod segments 314. A person of skill in the art will appreciate that a variety of techniques may be used to attach the end rod segments 314 to the central rod segment 312.

The end rod segments 314 are attached to fixation devices such as bone anchors 318. A person of skill in the art will appreciate that the bone anchors 318 may have a variety of configurations using the concepts of the invention.

In the preceding detailed description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting.

It is to be understood that other embodiments may be utilized and structural or logical changes may be made without departing from the scope of the present invention. The preceding detailed description, therefore, is not to be taken in a limiting sense, and the scope of the present invention is defined by the appended claims.

It is contemplated that features disclosed in this application, as well as those described in the above applications incorporated by reference, can be mixed and matched to suit particular circumstances. Various other modifications and changes will be apparent to those of ordinary skill.

The invention claimed is:

1. A scoliosis support rod system for treating scoliosis in a spine having a first vertebra and a second vertebra, wherein the scoliosis support rod system comprises:
   a central rod segment having a first end and a second end, wherein the central rod segment is deformable in response to a force placed thereon and wherein the central rod segment returns to an initial configuration when the force is discontinued;
   a first end rod segment having a first aperture formed therein, wherein the first aperture is adapted to slidably receive the first end of the central rod segment;
   a first bone anchor that is attachable to the first end rod segment, wherein the first bone anchor is attachable to the first vertebra; and
   a second bone anchor that is attachable to the central rod segment, wherein the second bone anchor is attachable to the second vertebra, wherein when the first bone anchor is attached to the first vertebra and the second bone anchor is attached to the second vertebra, a length of the scoliosis support rod system is adjustable by sliding the central rod segment with respect to the first end rod segment, wherein the slidable receiving of the first end of the central rod segment in the first aperture enables adjustment of a length of the scoliosis support rod system after implantation.

2. The scoliosis support rod system of claim 1, wherein the central rod segment is slidable and rotatable with respect to the first end rod segment when the first end of the central rod segment is inserted into the first aperture.

3. The scoliosis support rod system of claim 1, wherein the central rod segment is slidable but not rotatable with respect to the first end rod segment when the first end of the central rod segment is inserted into the first aperture.

4. The scoliosis support rod system of claim 3, wherein the first end of the central rod segment has a first profile, wherein the first aperture on the first end rod segment has a second profile and wherein the first profile is similar to the second profile.

5. The scoliosis support rod system of claim 1, and further comprising a second end rod segment having a second aperture formed therein, wherein the second aperture is adapted to slidably receive the second end of the central rod segment, wherein the second bone anchor is attachable to the second vertebra.

6. The scoliosis support rod system of claim 5, and further comprising an intermediate bone anchor that is attachable to a third vertebra, wherein the third vertebra is between the first vertebra and the second vertebra and wherein the intermediate bone anchor has a slot formed therein that is adapted to receive the central rod segment.

7. A scoliosis support rod system for treating scoliosis in a spine having a first vertebra and a second vertebra, wherein the scoliosis support rod system comprises:
   a central rod segment having a first end and a second end, wherein the central rod segment is deformable in response to a force placed thereon and wherein the central rod segment returns to an initial configuration when the force is discontinued;
   a first end rod segment having a first aperture formed therein, wherein the first aperture is adapted to slidably receive the first end of the central rod segment;
   a second end rod segment having a second aperture formed therein, wherein the second aperture is adapted to slidably receive the second end of the central rod segment;
   a first bone anchor that is attachable to the first end rod segment, wherein the first bone anchor is attachable to the first vertebra; and
   a second bone anchor that is attachable to the second end rod segment, wherein the second bone anchor is attachable to the second vertebra, wherein the slidable receiving of the first end of the central rod segment in the first aperture and the slidable receiving of the second end of the central rod segment in the second aperture enables adjustment of a length of the scoliosis support rod system after implantation.

8. The scoliosis support rod system of claim 7, wherein the central rod segment is rotatable with respect to the first end rod segment when the first end of the central rod segment is inserted into the first aperture.

9. The scoliosis support rod system of claim 7, wherein the central rod segment is not rotatable with respect to the first end rod segment when the first end of the central rod segment is inserted into the first aperture.

10. The scoliosis support rod system of claim 9, wherein the first end of the central rod segment has a first profile, wherein the first aperture on the first end rod segment has a second profile and wherein the first profile is similar to the second profile.

11. The scoliosis support rod system of claim 7, and further comprising an intermediate bone anchor that is attachable to a third vertebra, which is between the first vertebra and the second vertebra, wherein the intermediate bone anchor has a slot formed therein that is adapted to receive the central rod segment.

12. The scoliosis support rod system of claim 7, and further comprising a low friction bearing that extends over the first end of the central rod segment that is extendable into the first aperture.

13. A method of treating scoliosis comprising:
   providing a central rod segment having a first end and a second end, wherein the central rod segment is fabricated from an elastic material;
   attaching a first end rod segment to a first vertebra using a first bone anchor, wherein the first end rod segment has a first aperture formed therein;
   inserting the first end of the central rod segment into the first aperture on the first end rod segment;
   attaching the central rod segment to a second vertebra using a second bone anchor so that a force is placed on the central rod segment, wherein the force causes the central rod segment to deform from an initial configuration;
   sliding the central rod segment with respect to the first end rod segment; and
   transferring the force from the central rod segment to the first bone anchor and the second bone anchor, wherein the force on the first bone anchor and the second bone anchor causes the first vertebra to move away from the second vertebra, which reduces a curvature of a spine in which the first vertebra and the second vertebra are located such that the central rod segment returns to the initial configuration.

14. The method of claim 13, wherein transferring the force from the central rod segment to the first bone anchor and the second bone anchor causes the first vertebra to rotate with respect to the second vertebra.

15. The method of claim 13, wherein the central rod segment is slidable and rotatable with respect to the first end rod segment when the first end of the central rod segment is inserted into the first aperture on the first end rod segment.

16. The method of claim 13, wherein the central rod segment is slidable but not rotatable with respect to the first end rod segment when the first end of the central rod segment is inserted into the first aperture.

17. The method of claim 16, wherein the first end of the central rod segment has a first profile, wherein the first aperture on the first end rod segment has a second profile and wherein the first profile is similar to the second profile.

18. The method of claim 13, and further comprising
providing a second end rod segment having a second aperture formed therein;
inserting the second end of the central rod segment into the second aperture;
attaching the second end rod segment to the second vertebra with the second bone anchor so that the force is placed on the central rod segment, wherein the force causes the central rod segment to deform;
sliding the central rod segment with respect to the second end rod segment;
transferring the force from the central rod segment to the first bone anchor and the second bone anchor, wherein the force on the first bone anchor and the second bone anchor causes the first vertebra to move away from the second vertebra, which reduces the scoliosis.

19. The method of claim 18, and further comprising:
attaching an intermediate bone anchor to a third vertebra, wherein the third vertebra is between the first vertebra and the second vertebra
receiving the central rod segment in a slot formed in the intermediate bone anchor.

20. The method of claim 19, wherein the first bone anchor is attached to the first vertebra along a first initial axial alignment, wherein the intermediate bone anchor is attached to the third vertebra along a second initial axial alignment and wherein the first initial axial alignment is different than the second initial axial alignment.

* * * * *